United States Patent [19]
Suto et al.

[11] Patent Number: 4,731,725
[45] Date of Patent: Mar. 15, 1988

[54] DATA PROCESSING SYSTEM WHICH SUGGESTS A PATTERN OF MEDICAL TESTS TO REDUCE THE NUMBER OF TESTS NECESSARY TO CONFIRM OR DENY A DIAGNOSIS

[75] Inventors: Yasuzo Suto, Tochigi; Katsuyoshi Saito, Ootawara; Kenichi Sato, Kawasaki, all of Japan

[73] Assignee: Tokyo Shibaura Denki Kabushiki Kaisha, Kawasaki, Japan

[21] Appl. No.: 908,955

[22] Filed: Sep. 18, 1986

Related U.S. Application Data

[63] Continuation of Ser. No. 719,647, Apr. 5, 1985, abandoned, which is a continuation of Ser. No. 391,435, Jun. 23, 1982, abandoned.

[30] Foreign Application Priority Data

Jun. 24, 1981 [JP] Japan .................................. 56-96781

[51] Int. Cl.$^4$ ........................................... G06F 15/42
[52] U.S. Cl. .................................... 364/415; 364/413
[58] Field of Search ............... 364/200, 900, 415, 513, 364/413

[56] References Cited

U.S. PATENT DOCUMENTS

| T 916,007 | 11/1973 | Bonner | ................................ 364/200 |
| 4,158,200 | 6/1979 | Seitz et al. | ................................ 340/793 X |
| 4,259,725 | 3/1981 | Andrews et al. | ................................ 378/901 X |

OTHER PUBLICATIONS

"Radiology of the Abdomen: Impact of the New Imaging Methods", Ame. J. Rent., vol. 133, pp. 587–618, Whalen J. P., Oct. 1979.
"Integrated Imaging in Retropertoneal and Renal Disease", Japanese Journal of Clinical Urology, vol. 34, No. 7, pp. 615–627, Heshiki A., Jun. 1980.
"Integrated Body Imaging", Nagai, T. and Heshiki A., Maruzen, Tokyo, pp. 158–196, 1981.
"Critical Diagnostic Pathways in Radiology", pp. 1–44, 1981.
"Toshiba Medical Review", vol. 8, pp. 28–31, Jun. 1982.
Catanzarite, V. A. and Greenberg, A. G.; "*Neurologist*: A Computer Program for Diagnosis in Neurology", Proceedings of Computer Applications in Medical Care, IEEE, pp. 64–71, 1979.
Swenne, C. A. et al., "A Computerized, Interactive Coronary Care Unit Monitoring System", *IEEE Transactions on Biomedical Engineering*, Jan. 1977.

Primary Examiner—Gary V. Harkcom
Assistant Examiner—David L. Clark
Attorney, Agent, or Firm—Cushman, Darby & Cushman

[57] ABSTRACT

A data processing system for use in a total medical image diagnosis comprising a central processing unit, a first memory connected to the central processing unit for storing a plurality of types of fundamental data used for constructing a decision tree, a second memory connected to the central processing unit for storing various programs for constructing the decision tree, first data input system for inputting the fundamental data and the programs stored in the first and second memories into the central processing unit, circuitry for storing output data from the central processing unit and converting the output data into a bright signal for a display medical image, displaying for displaying a medical image corresponding to the bright signal from the storing and converting circuitry, a light pen connected to the central processing unit and operated by an operator for inputting a portion of the fundamental data displayed on the displaying means into the central processing unit as selected by the operator to construct a decision tree to perform a diagnosis, and a third memory connected to the central processing unit for storing the decision tree constructed with the selected fundamental data according to the program put in the central processing unit.

6 Claims, 11 Drawing Figures

DATA PROCESSING SYSTEM WHICH SUGGESTS A PATTERN OF MEDICAL TESTS TO REDUCE THE NUMBER OF TESTS NECESSARY TO CONFIRM OR DENY A DIAGNOSIS

This is a continuation of application Ser. No. 719,647, filed Apr. 5, 1985, which was abandoned upon the filing hereof, and which, in turn, is a continuation of Ser. No. 391,435, filed June 23, 1982, now abandoned.

BACKGROUND OF THE INVENTION

The present invention relates to a data processing system for use in a total medical image diagnosis which makes a proper combination of inspections of various types of medical images and sets up a proper order of executions of the inspections, and processes data on the result of the inspections.

In the recent years, X-ray CT (computed tomography) diagnostic devices have come into wide use. With this, more valuable medical images than those obtained by the conventional X-ray photographic diagnostic devices and the nuclear medicine diagnostic devices have been provided to remarkably improve the medical image diagnosis technology.

Four types of diagnostic devices provide different image information. The X-ray photographic medical image is two dimensional with a high accuracy, the CT medical image is anatomical and three dimensional, the ultrasonic medical image provides information effective for observing the soft part tissue and the motion tissue, and the nuclear medicine medical image is effective for studying the physiological function.

In the field of medical image diagnostic medicine, an increasing number of the different and further detailed information on the diagnosis is available, in addition to the medical image information provided by the above four imaging devices.

Recently, in addition to the X-ray CT, radiation emission CTs, using isotope, are being used, which have features of both the CT medical image and the nuclear medicine medical image.

An NMR (nuclear magnetic resonance) CT, recently attracting attention, has been studied and will be put into practice in a near future.

In the X-ray photographic diagnostic device, there are two photographies, a general (plain) photography and a cytography. In the cytography, there is established a plain cytography for digestive organs and many other special cytographies using catheter for the circulating system. These photographies provide many types of medical image information.

In digestive system diagnoses, microscopic medical image information with an endoscope using a gastor-camera, an endoscope television camera, is very important.

Diagnosis by thermography has frequently been used recently, in which a temperature distribution over the body surface is provided in the form of a medical image, and is used to find a disease.

To make a diagnostic judgement, a doctor studies the medical image information as mentioned above and selects desired medical image information from these pieces well suitable for diagnosing the disease.

Each type of medical image information has unique features as mentioned above. It is almost impossible, however, that an accurate and reliable diagnosis of a disease can be based solely on the information provided by a single specific medical image. To obtain a more accurate diagnosis, a so-called total medical image diagnosis has recently been proposed, in which different types of medical image information are combined for diagnosing one disease.

The total medical image diagnosis, however, involves two problems. One problem is deciding which valuable medical images must be selected from the many medical images, how to combine inspections of the medical images to obtain the medical image information, and in what order the inspections of the medical images must be executed. The other problem is how to obtain a more valuable composite information from the medical images. In connection with the former problem many clinical examples on specific diseases have been disclosed.

In performing the total medical image diagnosis, a so-called decision tree (D-T) describing routine procedural steps, as shown in FIG. 1, is frequently used. More particularly, a doctor anticipates a kind of a disease on the basis of the clinical data obtained by interviewing a patient, by biopsy, electrocardiogram etc. In this example the anticipated disease is pancreatic mass. In a level 1 of the medical image inspection, an X-ray medical image on a plain film is obtained. If the doctor is confident in a level 2 that the diseased part is normal or abnormal, the diagnosis process ends through only the level 1. When he can not determine whether it is normal or not, in the level 2, that is, when the diseased part is doubtful, a level 3 of the medical image inspection is executed. In the level 3, it is assumed that a size of the diseased part is found by the doctor below a border line size which is insufficient for exactly inspecting the diseased part, because the diseased part is very large. In this case, the doctor advances the inspection of the medical image to a level 4. In the level 4, ERCP (endoscopic retrograde cholangic pancreatography) is executed. In the level 3, also when a vascular tumor of 2 cm or more is found in the artery, the medical image inspection is advanced to the level 4. In the level 4, in this case, the arteriograph is taken to have an arteriogram. Further, when the examination in the level 3 shows that the diseased part is made of motion tissue and its medical image has a motion artifact to disable the inspection of the diseased part, the inspection advances to the level 4 where the ultrasonograph is taken.

The inspection system has a four level construction in which the inspection steps are classified into four levels. The inspection steps are advanced in the order of level 1, 2, 3 and 4. The inspection step of the level 1 is first applied to roughly determine what part is affected. Following the inspection of the level 1, the judgements are made in the levels 2 and 3. A proper inspection is carried out in the level 4 in accordance with the result of the judgements.

As described above, the doctor diagnoses by using a D-T to properly combine the medical image inspections.

However, there are many kinds of the medical image examinations requiring highly skilled techniques. In constructing or forming a D-T and executing the diagnosis on the basis of a D-T, complicated work for interrelating a large amount of information must be done. Further, for the combination of the medical image inspections and the order of the inspections in their execution, doctors have different views. Therefore, it is problematic and not practical to uniformly construct a D-T. In the data processing system for use in a total medical image diagnosis of the present invention, however, thoughts of respective doctors can be reflected with respect to an inspection of a diseased part.

SUMMARY OF THE INVENTION

Accordingly, an object of the present invention is to provide a data processing system for use in total medical image diagnosis, which can provide an improved total medical image diagnosis, and which can most effectively achieve the construction of a decision tree for a total medical image diagnosis, the execution of inspections according to the D-T formed, and the processing of the data obtained as the result of the inspections.

According to the present invention, there is provided a data processing system for use in a total medical image diagnosis comprising a central processing unit, a first memory connected to the central processing unit for storing a plurality of types of fundamental data used for constructing a decision tree, a second memory connected to the central processing unit for storing various types of programs for constructing the decision tree, first data input means connected to the central processing unit for inputting the fundamental data and the programs stored in the first and second memories into the central processing unit, means connected to the central processing unit, for storing output data from the central processing unit and for converting the output data into a bright signal for displaying medical image, displaying means connected to the storing and converting means for displaying a medical image corresponding to the bright signal from the storing and converting means, second data input means connected to the central processing unit and operated by an operator for inputting a portion of the fundamental data displayed on the displaying means into the central processing unit as selected by the operator to construct a decision tree to perform a diagnosis, and a third memory connected to the central processing unit for storing the decision tree constructed using the selected fundamental data according to the programs put in the central processing unit.

DETAILED DESCRIPTION OF THE PREFERRED EMBODIMENTS

Figure 2:
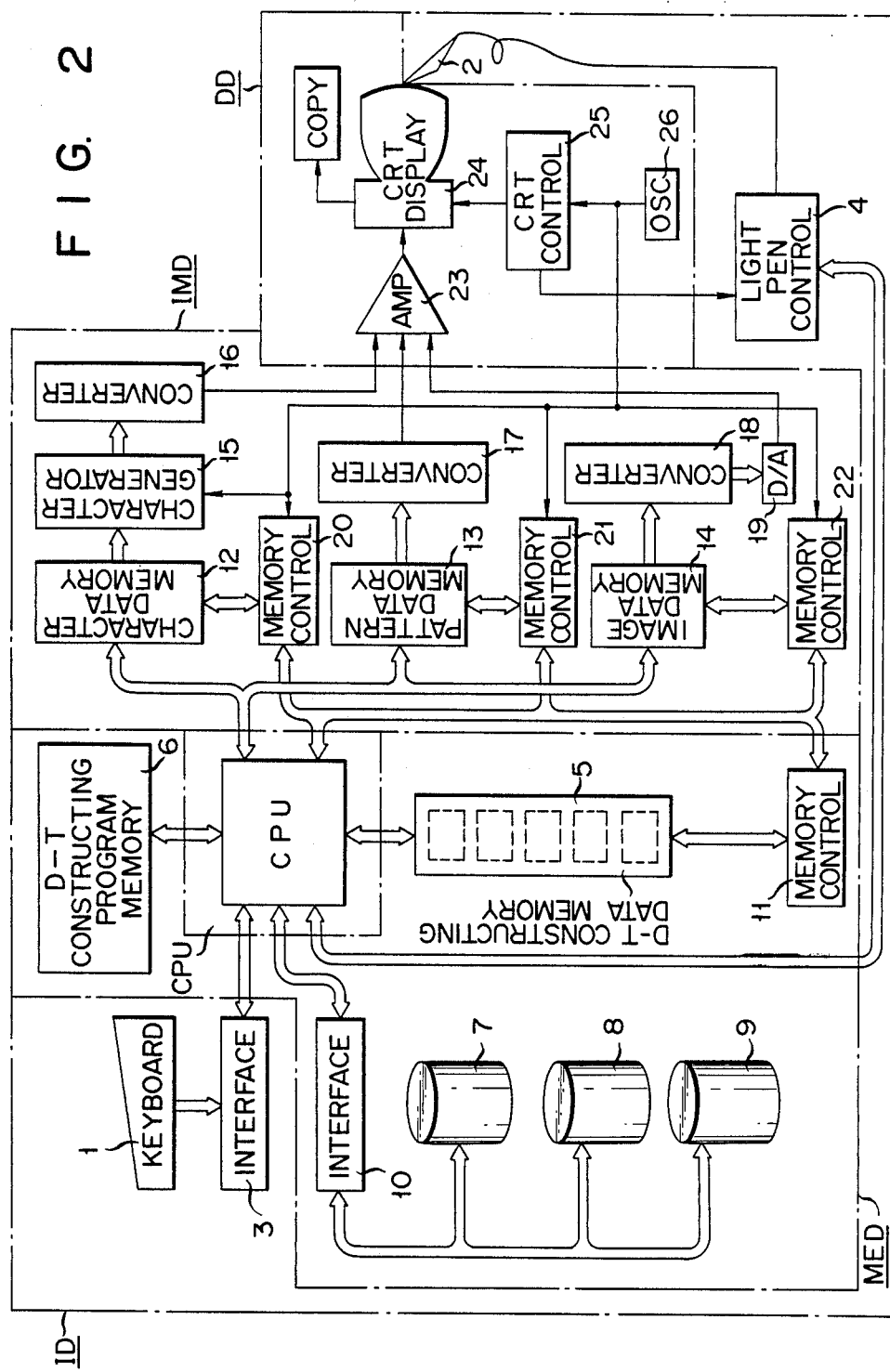
FIG. 2 is a block diagram of an embodiment of a data processing system for use in a total medical image diagnosis according to the present invention.

Referring to FIG. 2, there is shown a data processing system for use in a total medical image diagnosis according to the present invention.

An input device ID for keying in various types of data into the data processor by a doctor is provided with a keyboard 1 and a light pen 2. The keyboard 1 is connected through an interface 3 to a central processing unit (CPU) and the light pen 2 is connected to the same through a control device 4.

A memory device MED is comprised of a D-T constructing memory 5 such as a floppy disc or a magnetic bubble memory, a D-T constructing memory 6 as a semiconductor memory such as a programmable read only memory (PROM) of a random access memory (RAM), a large capacity memory 7 such as a magnetic disc for storing D-T registering data and diagnosis planning data, a memory 8 for storing medical image data resulting from the inspection of the medical images, and a memory 9 for storing data other than the medical image data of the data obtained by the clinic inspection. The memories 7, 8 and 9 are external memories and coupled with CPU through an interface 10. A memory control device 11 receives instructions from CPU and controls the data memory 5 for D-T construction. The remaining memories 6 to 9 are also provided with the memory control devices, although not illustrated, for simplicity.

A data memory device IMD for medical image displaying, receiving various types of data through CPU, is comprised of a character data memory 12 such as a 512 ×512 matrix memory (referred to as a first medical image memory), a pattern data memory 13 for displaying a graphic pattern for constructing a D-T (referred to as a second medical image memory), which has a similar construction to the first medical image memory, and an image data memory 14 for displaying inspected medical image (referred to as a third medical image memory). The first medical image memory 12 is connected to a gray level converter 16 as a ROM, for example, through a character generator 15 for generating characters of the input data received, which are in the form of digital data. The second and third medical image memories 13 and 14 are coupled with gray level converters 17 and 18, respectively. The gray level converters 16, 17 and 18 convert the input data into a corresponding gray signal. The converter 18 is connected to a digital to analog (D/A) converter 19. Memory control devices 20 to 22 are under control of CPU to control the first to third medical image memories 12 to 14, respectively.

A display device DD for displaying medical image data from IMD is comprised of a video amplifier 23 coupled at the input with output signals from the converters 16 and 17 and the D/A converter 19, a CRT display unit 24 for displaying the medical image data on the output signal from the video amplifier 23, which is a 20-inch CRT capable of displaying characters in a 80×50 matrix, a CRT control device 25 for applying a control signal to the CRT display unit 24 and the light pen control device 4, and a clock pulse generator OSC 26 for applying a reference control signal to the CRT control device 25 and a read/write timing signal to the memory control devices 20 and 21 and the character generator 15.

Figure 3:
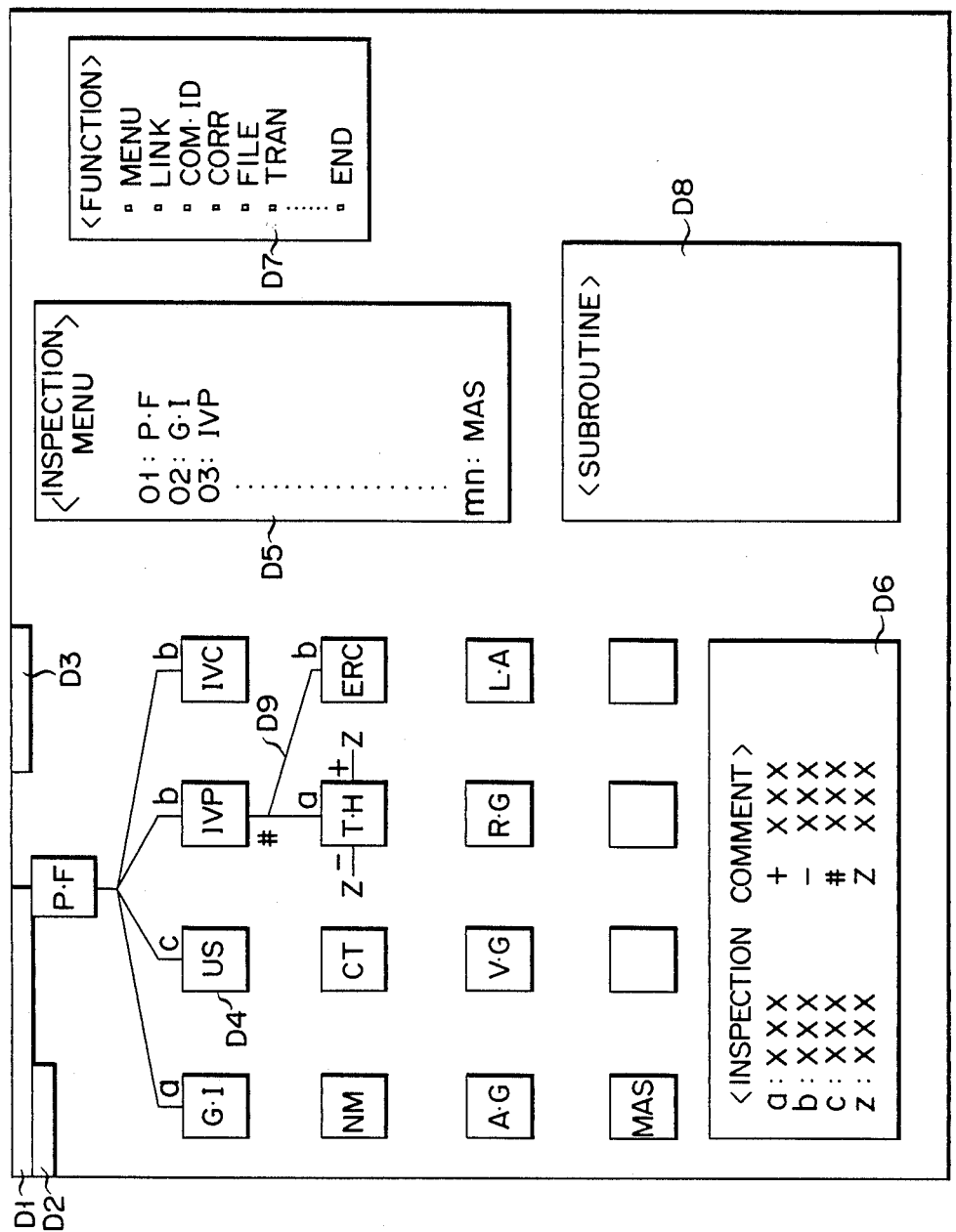
FIG. 3 illustrates a display on a CRT displaying a graphic pattern for preparing a D-T and various types of fundamental data.

The data memory 5 stores various types of pattern data, as shown in FIG. 3. Displayed as pattern data are the name of a D-T designated as D1 (specifying data of the display area), date D2 of D-T construction (specifying data of the display area), code D3 of the D-T (specifying data of the display area), box D4 in which the name of the medical image inspection is inserted, medical image inspection menu D5 (specifying data of the display area, character codes of the title and various inspections), inspection comment D6 (specifying data of the display area, character codes of the title and comment), function list D7 (specifying data of the display area, character codes of the title and the menu) subroutine menu D8 (specifying data of the 25 display area, character codes of the title and the menu), and lines D9 connecting the boxes (specifying data of the display area, and line patterns). The abovementioned data are displayed on the CRT display during the course of forming a D-T.

An execution program for processing data on the basis of the signal from the keyboard 1 and the light pen 2 is stored in the memory 6.

The following explanation is how to execute the total medical image diagnosis using the diagnosis data processing system thus constructed.

Figure 1:
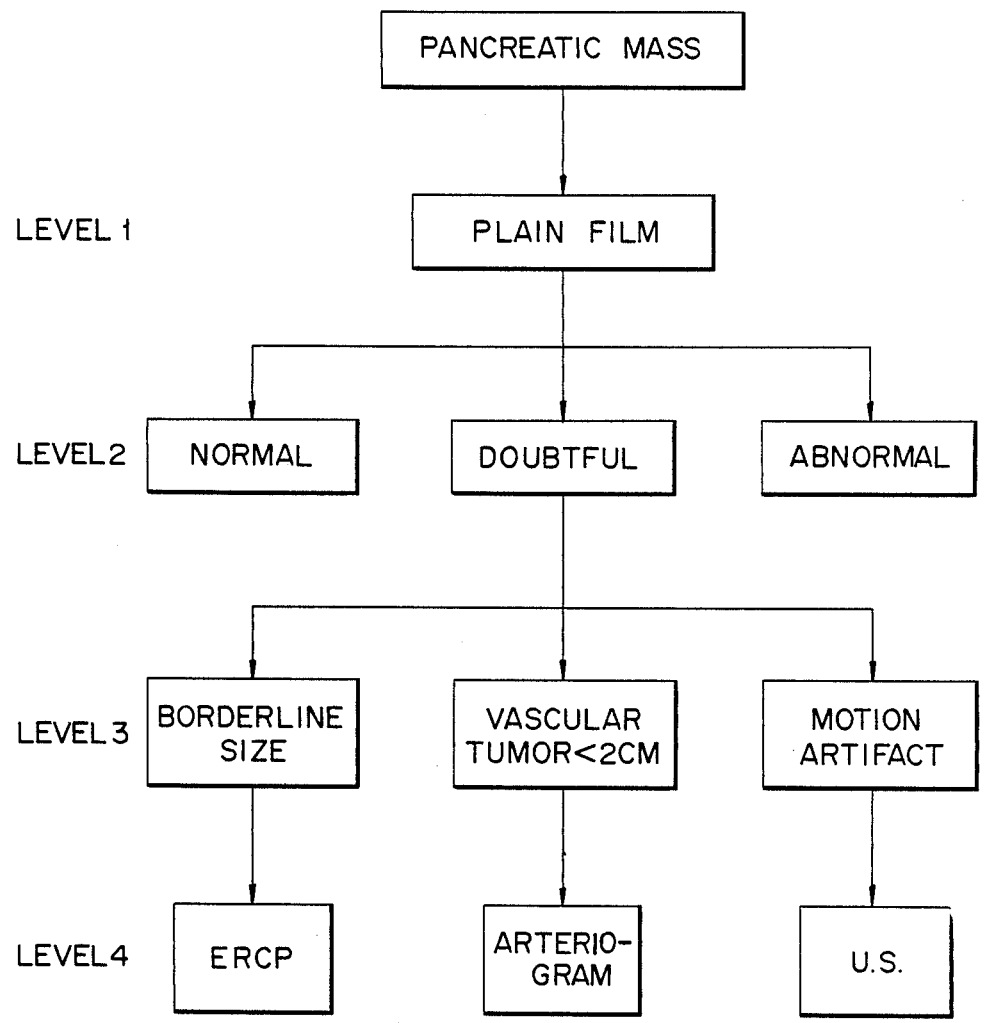
FIG. 1 illustrates an example of a decision tree.

The formation of the D-T shown in FIG. 1 will be described. A doctor operates the related keys to input the data D5 to D8 into the first medical image memory 12 and the data D4 (box) into the second medical image memory 13, respectively, through CPU from the data memory 5. The data transferred to the first medical image memory 12 is applied to the CRT display unit 24, via the character generator 15, the gray level converter 16 and the video amplifier 23. The data transferred to the second medical image memory 13 is applied to the CRT display unit 24 through the gray level converter 17 and the video amplifier 23. These data are displayed on the CRT, as shown in FIG. 3.

The operator further operates the keyboard 1 to key in the object of diagnosis and the name of a disease (in this example, PANCREATIC MASS) which are transferred to the CRT display 24, through the CPU, the first memory 12, the character generator 15, the gray level converting circuit 16, and the video amplifier 23. The name of the disease is displayed on the upper left part on the CRT screen (D1 in FIG. 3).

Then, the operator picks up by means of the light pen 2 "MENU" from the function list (D7) and selects a proper inspection menu from the inspection MENU list (D5), and inserts it into the box (D4). In more particular, the operator picks up "MENU" in the function list D7 displayed on the CRT screen by means of light pen 2, and picks up the name of an inspection to be executed, such as PF (plain film), B.E (barium enema), G.I (gastrointestinal), IVP(intravenous pyelography ), IVC(intravenous cholecystography), CT (computed tomography), and US (ultrasonography), or picks up the serial No. 01, 02, 03, . . . or mn attached to the inspection name. Succeedingly, a fringe of the box to be allotted is picked up. Through this operation, the inspection name specified is displayed in the boxes.

Then, "LINK" in the function list D7 is picked up by the light pen 2 and the box containing the first inspection name (P.F.) is picked up. Following the first inspection, the box containing the name of the second inspection to be executed is picked up. Then, both the boxes are connected by the line D9. In case where the second inspection is branched into a plurality of inspections such as G.I, US, IVP and IVC, proper comments on the selection of the branched inspections are placed on the boxes. Specifically, symbols +(normal), −(abnormal), #(doubtful), Z(stop), a(borderline), b(vascular tumor <N cm), c(motion artifact), etc., as shown in the lower left part of the CRT screen, are placed above the boxes enclosing the inspection names. For example, to indicate the borderline size as the inspection result of the level 1 to execute G.I., the box enclosing the inspection name G.I. and the symbol a (indicating the borderline) of the inspection comment are picked up in succession. By attaching the symbol to each of the boxes, it is easy to find the inspection to be executed of those branched second inspections. When the second inspection, for example, IVP, can not provide a sure diagnosis, the third inspection is executed in a similar manner to the second inspection. In this case, the boxes of the second inspection (IVP in FIG. 3) and the third inspection (for example, T.H. and ERC) are connected by the lines, and the inspection comment for the branch to the third inspection is attached to each of the third inspections.

To erase the data once stored and store the new data in place of the old data, that is to say, to correct the data, "CORR" is picked up from the function list D7, and then the data to be corrected is picked up by the light pen and erased, and the new data is stored into the memory.

Through the operation as mentioned above, the D-T is formed.

The next operation is to file the D-T thus formed. In filing the D-T, "FILE" in the function list D7 is picked up by the light pen 2. The next operation is to file the D-T thus formed. For filing the D-T, "FILE" in the function list D7 is picked up. Then, the keyboard 1 is operated to key in date of forming the D-T (D2 of FIG. 3), and code of D-T (D3). Following this "TRAN" in the function list D7 is picked up by the light pen 2 to store the D-T formed into the external memory 7. In this way, the filing of D-T is performed.

Figure 4:
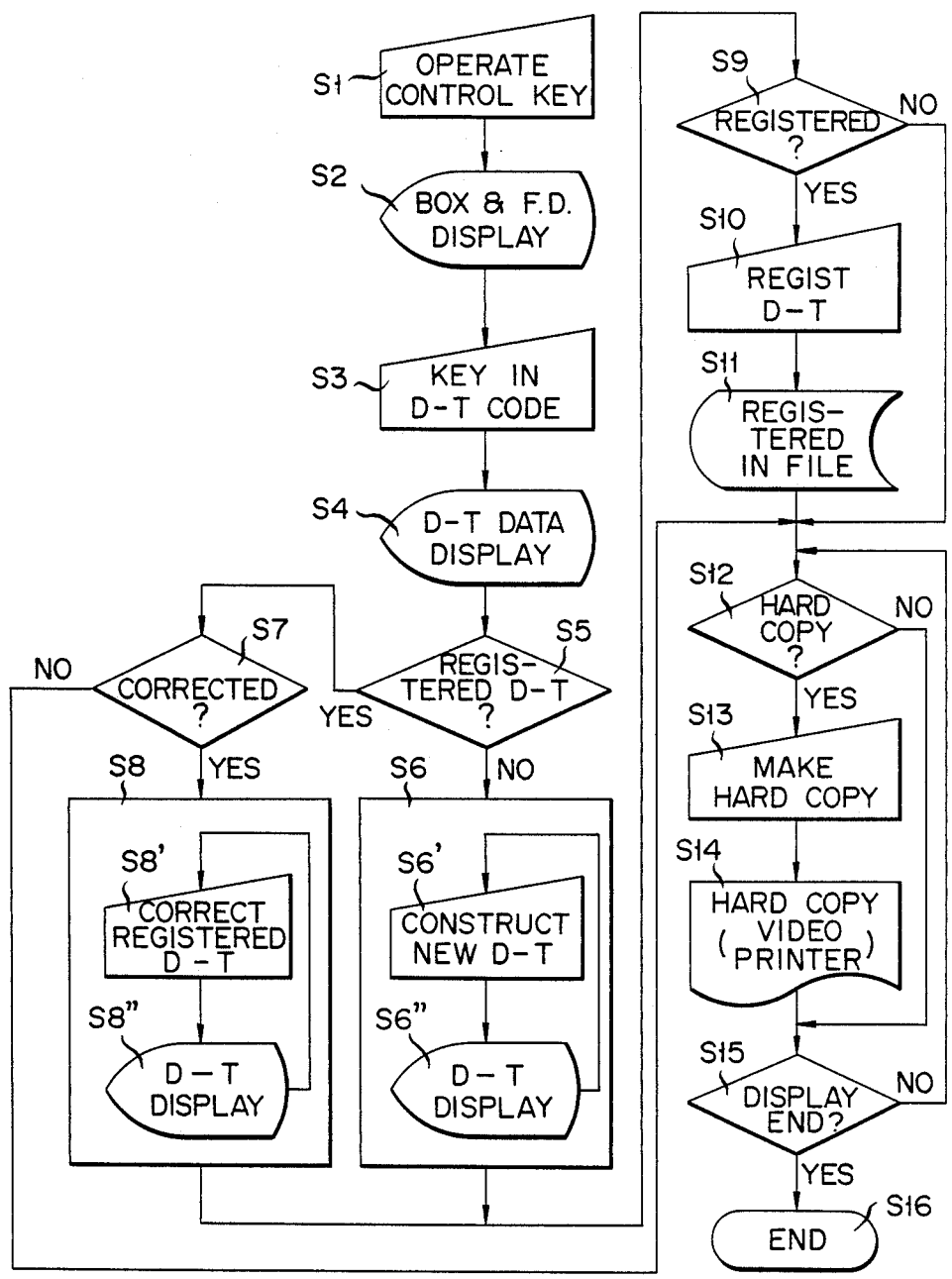
FIG. 4 shows a flow chart illustrating a routine for filing, correcting and using the D-T.

A routine for forming the D-T, filing the D-T formed, and using the D-T filed is as shown in FIG. 4. This routine will be described in detail referring to FIG. 4.

In a first step (S1), the keyboard 1 is operated. In a second step (S2), fundamental data for D-T formation such as boxes and function list are displayed on the screen of the CRT display 24. In a third step (S3), a code of the D-T required for a disease is keyed in by operating the keyboard 1. In the fourth step (S4), the D-T is displayed on the CRT display 24. In this case, when no D-T is displayed, the D-T has not been registered. On the other hand, when it is displayed, the D-T has been registered (S5). When the D-T is not displayed, a new D-T is constructed (S6). In this case, as described above, the D-T is formed on the basis of a display (S6'') on the CRT screen by using the keyboard 1 and the light pen 2 (S6'). When, on the other hand, the D-T is registered, it is checked whether the registered D-T must be corrected or not (S7). When the correction is needed, the correction work (S8) is performed on the basis of a display (S8'') on the CRT screen by using the keyboard 1 and the light pen 2 (S8'). The doctor judges whether the newly formed or corrected D-T shall be registered or not (S9). If the registration is allowed, the D-T is registered into the memory 7 (S11) using the keyboard 1 or the light pen 2 (S10). Then, the doctor judges whether the hard copy of the D-T is needed or not (S12). If the hard copy is needed, the operation for forming the hard copy is performed (S13). The hard copy is formed by a video printer etc., for example (S14). When the display must be continued (S15), the doctor keeps the CRT display 24 in the display mode. When the display becomes unnecessary, the keyboard 1 is operated to erase the display on the CRT screen by operating the keyboard 1 (S16).

Figure 5:
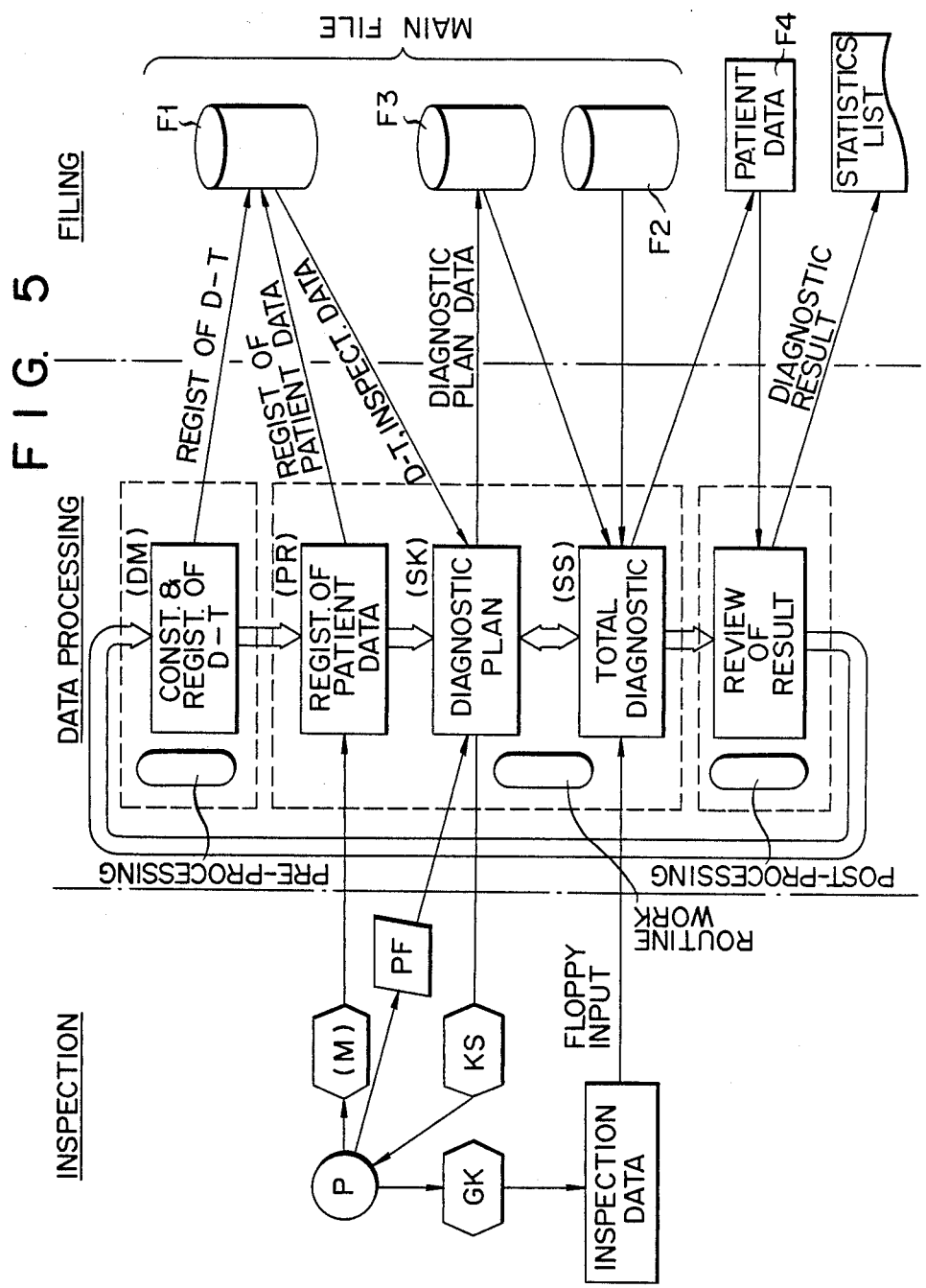
FIG. 5 shows an explanatory diagram for illustrating procedural steps of an total medical imaging for a total medical image diagnosis.

There will be described procedural steps for executing the total imaging diagnosis of a disease by using the D-T prepared for each disease and filed referring to FIG. 5.

The procedure steps on the total medical imaging is comprised of a inspection step, a data processing step, and a filing step. The inspection step includes various inspections applied to a patient depending on the judgement by a doctor. In the data processing step, data processing is performed using the result of the inspection and the D-T relating to a disease anticipated. In the filing step, D-T for each patient, statistical lists and the like are filed.

For diagnosing a patient according to the total medical image diagnosis, clinic inspections (M) such as the interview with the patient and the biochemistry inspection, etc., are performed. The data obtained by the inspection, as patient's data, are filed into the external memory F1. The doctor anticipates a disease of the patient on the basis of the patient's data and makes his diagnosing plan. To this end, the doctor reads out the D-T corresponding to the anticipated disease from the external memory F1. When there is no need for correcting the D-T read out from the external memory F1 with relation to the state of the disease, the D-T is stored back into the memory F1 as the patient's data. When the D-T must be corrected, it is stored into the memory F1 after the D-T is corrected. The doctor forms an inspection directory sheet (KS), and performs the medical image inspection (GK) according to the directions in the sheet. In executing the medical image inspection, the doctor gives a proper judgement on the disease every time each inspection is completed. Further, he judges as to whether the further inspection is necessary or not, and if necessary, he also judges what inspection is selected, and whether or not any comment is given to the inspection to next be performed. On the judgement, he progressively operates related keys. As described above, the doctor makes his decision on the diagnosis on the basis of the result of the inspections, and selects the inspection to next be executed depending on his decision. Thus, the doctor proceeds with his inspection for diagnosis while talking with the data processor. The medical images obtained by the medical image inspections such as a CT image, a US image, an NM image, an X-ray image, etc., are filed in the external memory F4 (corresponding to the external memory 8 in FIG. 2). At the time of diagnosis, these data are read out together with the diagnosis plan data, each-patient data. In the course of executing the inspection, inspection data other than the medical image data, such as electrocardiogram, are read out from the external memory F2 and complementally used for the medical image data to improve an accuracy of the diagnosis. In this way, the diagnosis is performed for each patient.

Figure 6:
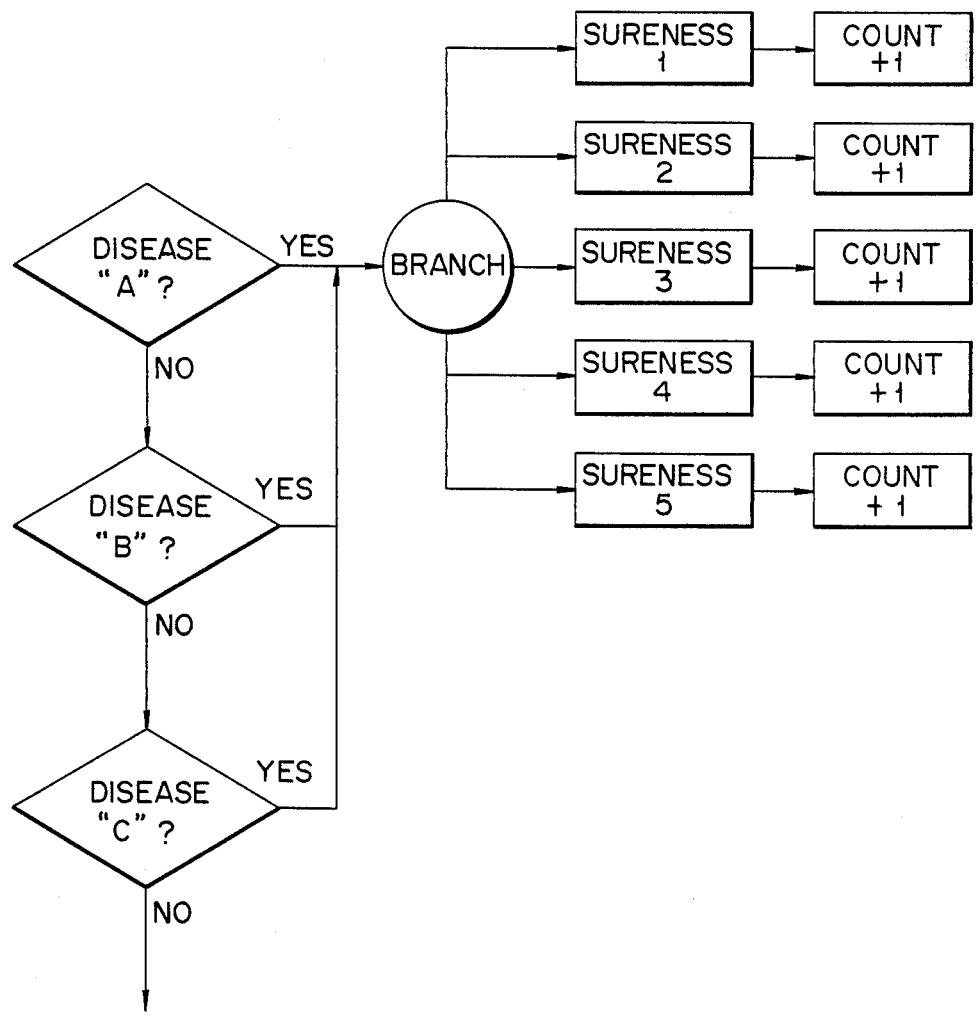
FIG. 6 shows a flow chart for executing a sureness diagnosis.
Figure 7A:
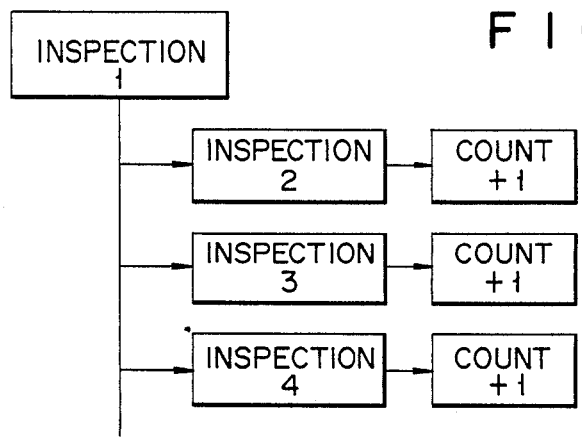
FIGS. 7A to 7C show flow charts for executing branch totalizing of the D-T.
Figure 7B:
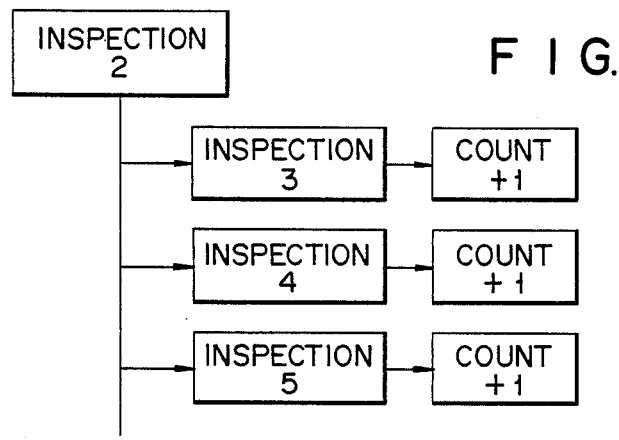
Figure 7C:
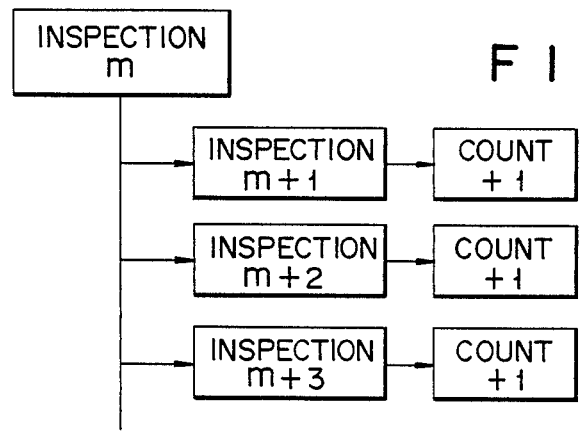

After the diagnostic procedure ends, the result of the diagnosis is statistically processed and evaluated. For example, a statistical analysis or branch totalizing of the D-T is carried out based on the result of the real diagnosis. Then, the D-T is corrected according to the analysis or totalizing result. For example, a sureness of one inspection is checked for the type of one disease. In the sureness check, it is checked, as shown in the flow charts of FIG. 6, at what degree of sureness the result of one inspection could anticipate the disease. Assume now that the doctor could diagnosis a diseased part of a patient as a disease A, on the basis of the inspection by, for example, the CT. For checking the sureness of the diagnosis, the sureness is classified into 5 ranks, 1st to 5th ranks. When the sureness is relatively high, or in the 4th or 5th rank, the related counter is incremented by one. The CT inspection, for example, is applied for a plurality of patients. Then, the contents of the related counters are checked. If the contents of the counter with high sureness degree is relatively large, it is considered that the inspection by the CT is suitable for the diagnosis of the disease A. Conversely, when the contents of the counter with low sureness is high, it is judged that CT inspection is not suitable for the diagnosis of the disease A. The same thing is correspondingly applied for the other diseases B and C. Further, this method is applied for other inspections than the CT inspection. The branch totalizing of the D-T is a statistical process to determine in what order various types of inspections specified by the D-T has been performed in the diagnosis. A flow chart as shown in FIG. 7A is used for executing the branch totalizing. This totalizes the result of the inspection following the inspection 1. If that inspection is an inspection 2 of those inspections in the same level, the corresponding counter is incremented by 1. If it is an inspection 3, the corresponding counter is incremented by one. Similarly, if the inspection following the inspection 3 is an inspection 3 of those in the same level, the corresponding counter is incremented by one, as shown in the flow charts of FIG. 7B. If it is the inspection 4, the corresponding counter is incremented by one. As for the subsequent inspections 3, 4. . . . , m, ,m+1, m+2, . . . , the similar process is performed. The inspection following one inspection is statistically obtained based on the result of the branch totalizing (FIG. 7C).

In correcting the D-T, the statistically totalized result is accumulated for a given period of time, for example, one month, half year, and one year. The result of the accumulation is used for the D-T correction. For example, the inspection 1 is applied to 100 clinical cases of the disease A. If the result of these in spection shows 5 cases with the sureness 1, a ratio of the sureness 1 for the inspection 1 is 5%. The ratio of all the surenesses is obtained on all the inspections. The results of the diagnoses are accumulated for each inspection and each sureness on each disease, and their ratios are obtained. From the result of the branch totalizing of D-T, the types of the inspections following one inspection, or the number of the branches, are accumulated and the branch ratios of the inspections following one inspection are obtained.

From the result of the accumulation, it is seen what inspection can provide the most reliable diagnosis for one disease, and further what inspection is best for the inspection to next be executed in order to ensure an accurate and effective diagnosis.

Figure 8:
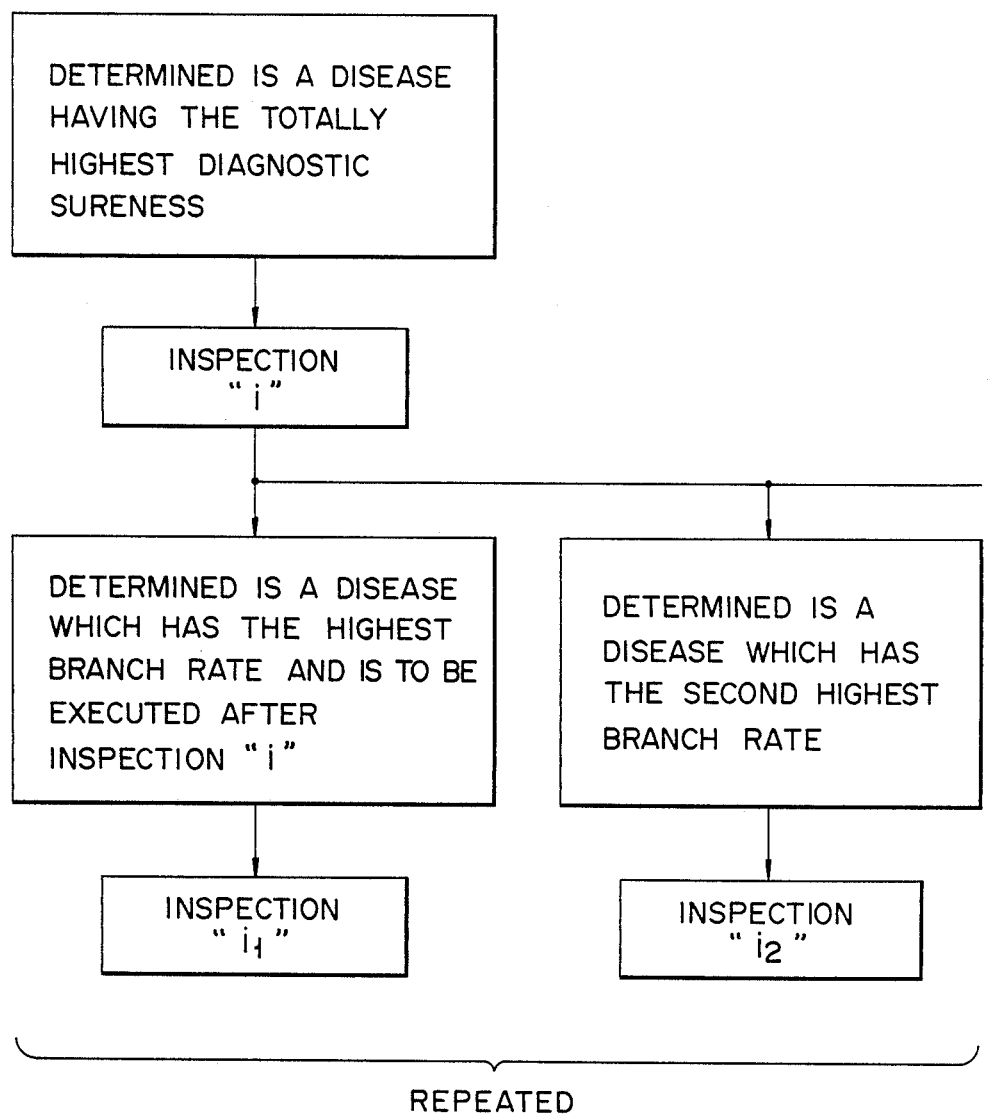
FIG. 8 shows a flow chart for correcting a structure of the D-T.

The D-T correction is made by executing the process as given by a flow chart shown in FIG. 8, on the basis of the statistical data formed as mentioned above.

In summary, the inspection "i" of which the diagnosis probability is totally highest for the anticipated disease is obtained, and then the inspection "$i_1$" of which the branch ratio is highest is successively obtained for the successing inspections. As a result, the doctor can form a D-T with high accuracy which can be processed for a short time.

Figure 9:
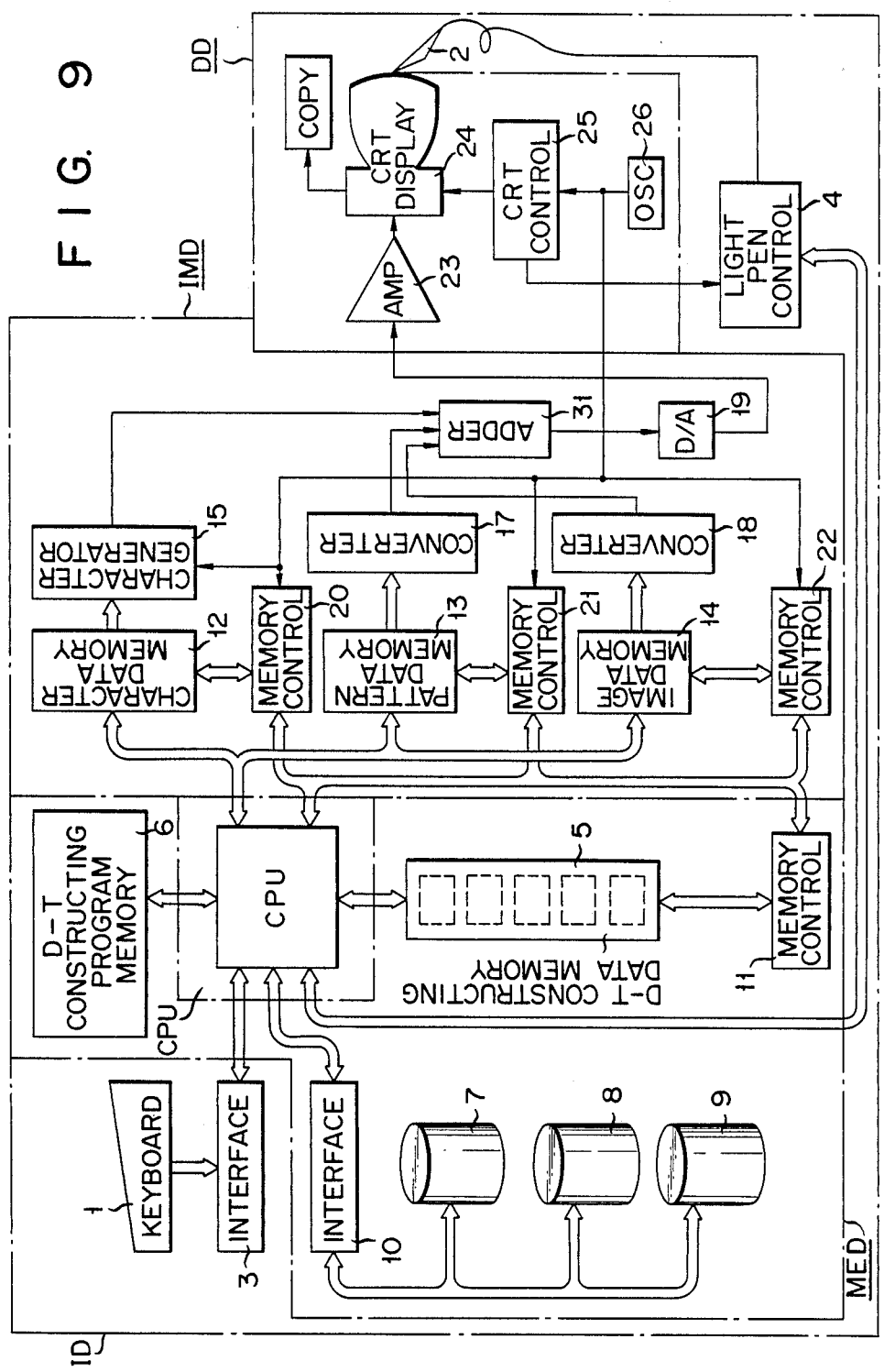
FIG. 9 shows a block diagram of another embodiment of a data processing system for use in total medical image diagnosis according to the present invention.

Turning now to FIG. 9, there is shown another embodiment of a data processing system according to the present invention. In this embodiment, the arrangement of the conversion and memory section IMD is slightly modified. Output signals from the character generator 15, and the converters 17 and 18 are applied to an adder 31 where these are summed. The output signal from the adder 31 is applied to the D/A converter 19 where it is converted into an analog signal, and then applied to the video amplifier 23. The converter 16 is not provided. The remaining portion of the circuit arrangement is the same as that of the FIG. 2 embodiment.

As seen from the foregoing description, the formation of a D-T for the total medical image diagnosis, the execution of the inspections according to the D-T formed, and the diagnosis on the basis of the result of the inspections are performed by a doctor while he is talking with the data processor. Accordingly, the various works and data processing on the inspections are made effective as high as possible, thus improving a diagnosis accuracy in the total medical image diagnosis.

The input devices such as the key board and the light pen may be replaced by a voice input device. While specific embodiments have been described, the present invention is not limited by the above-mentioned embodiments but may be modified variously within the scope of the present invention.

What we claim is:

1. A data processing system for identifying a sequence of diagnostic procedural steps for using medical diagnostic apparatus to generate, for an operator, information to confirm or reject a diagnosis hypothesis, said sequence minimizing said procedural steps before said diagnosis hypothesis can be confirmed or rejected comprising:

means for storing data representing decision tree elements required to construct a decision tree indicating a predetermined combination and order of medical inspections, said medical inspections generating information which said operator uses to confirm or reject a diagnosis hypothesis corresponding to any of a plurality of diseases;

means, coupled to said storing means, for assembling said data to construct a decision tree of medical inspections, said medical inspections generating information to confirm or reject a particular diagnosis hypothesis;

means, coupled to said storing means and said assembling means, for allowing said operator to enter a degree to which each of said medical inspections in said constructed decision tree minimized said procedural steps in confirming or rejecting said particular diagnosis hypothesis and for generating statistical indications of said degree of minimizing said procedural steps for each of said medical inspections;

said assembling means also being for modifying said constructed decision tree, based on said statistical indications, to minimize the number of said medical inspections which said operator uses, to confirm or reject said particular diagnosis hypothesis; and means, coupled to said assembling means for indicating visual information corresponding to data signals of said constructed decision tree of medical inspections supplied from said storing means and said assembling means.

2. The system according to claim 1, wherein said storing means comprises a first memory for storing a plurality of types of fundamental data used for constructing a decision tree.

3. The system according to claim 2, wherein said assembling means comprises a third memory coupled to said first memory for storing a decision tree constructed using said fundamental data from said first memory.

4. The system according to claim 3, wherein said indicating means comprises means coupled to said assembling means and said storing means for storing output data from said assembling means and said storing means and converting the output data into a bright signal for displaying information; and displaying means coupled to said storing and converting means for displaying a medical image corresponding to the bright signal from the storing and converting means.

5. The data processing system according to claim 3, wherein said allowing means comprises first data input means for inputting the fundamental data for said first memory; and second data input means, operated by an operator, for inputting a portion of the fundamental data displayed on said displaying means as selected by the operator to construct a decision tree to perform a diagnosis, and wherein said indicating means includes a fourth memory, coupled to said assembling means and said storing means, for storing character data from said assembling means and said storing means, means, coupled to said fourth memory, for causing said character data to be stored in said fourth memory, first converter means, coupled to said fourth memory for converting the character data stored in said fourth memory into data representative of a corresponding gray level, a fifth memory, coupled to said assembling means and storing means, for storing graphic pattern data from said assembling means and said storing means, means, coupled to said fifth memory, for causing said graphic pattern data to be stored in said fifth memory, second converter means, coupled to said fifth memory, for converting the graphic pattern data stored in said fifth memory into data representative of a corresponding gray level, a sixth memory, coupled to said assembling means and said storing means, for storing medical image data from said assembling means and said storing means, means, coupled to said sixth memory, for causing said medical image data to be stored in said sixth memory, said third converter means, coupled to said sixth memory, for converting the medical image data stored in said sixth memory into data of a corresponding gray level.

6. The data processing system according to claim 5, wherein said indicating means includes a fourth memory, coupled to said assembling means and said storing means, for storing character data from said assembling means and said storing means, means, coupled to said fourth memory, for causing said character data to be stored in said fourth memory, a character generator, coupled to said fourth memory for converting the character data stored in said fourth memory into a digital signal, a fifth memory, coupled to said assembling means and said storing means, for storing graphic pattern data from said assembling means and said storing means, means, coupled to said fifth memory, for causing said graphic pattern data to be stored in said fifth memory, first converter means, coupled to said fifth memory, for converting the graphic pattern data stored in said fifth memory into data of a corresponding gray level, a sixth memory, coupled to said assembling means and said storing means, for storing medical image data from said assembling means and said storing means, means, coupled to said sixth memory, for causing said medical image data to be stored in said sixth memory, second converter means, coupled to said sixth memory, for converting the medical image data stored in said sixth memory into data of a corresponding gray level, an adder coupled to said character generator and both said converter means, for adding the output data from said character generator and both said converter means, and a digital to analog converter, coupled to said adder, for converting an output signal from said adder into an analog signal.

* * * * *